(12) United States Patent
Van Breugel et al.

(10) Patent No.: US 9,234,214 B2
(45) Date of Patent: Jan. 12, 2016

(54) FERMENTATION PROCESS AT REDUCED PRESSURE

(75) Inventors: Jan Van Breugel, Woudrichem (NL); Willem Jacob Groot, Dordecht (NL); Peter Paul Jansen, Oss (NL)

(73) Assignee: Purac Biochem BV, Gorinchem (NL)

(*) Notice: Subject to any disclaimer, the term of this patent is extended or adjusted under 35 U.S.C. 154(b) by 478 days.

(21) Appl. No.: 13/501,369

(22) PCT Filed: Oct. 14, 2010

(86) PCT No.: PCT/EP2010/065395
§ 371 (c)(1),
(2), (4) Date: Jun. 12, 2012

(87) PCT Pub. No.: WO2011/045365
PCT Pub. Date: Apr. 21, 2011

(65) Prior Publication Data
US 2012/0244587 A1 Sep. 27, 2012

(30) Foreign Application Priority Data
Oct. 14, 2009 (EP) .................................... 09172984

(51) Int. Cl.
| C12P 7/42 | (2006.01) |
| C12P 7/56 | (2006.01) |
| C12P 1/00 | (2006.01) |
| C12P 7/46 | (2006.01) |
| A61K 38/00 | (2006.01) |

(52) U.S. Cl.
CPC ... *C12P 1/00* (2013.01); *C12P 7/46* (2013.01); *C12P 7/56* (2013.01)

(58) Field of Classification Search
CPC .................................................. Y10S 435/813
See application file for complete search history.

(56) References Cited

U.S. PATENT DOCUMENTS

| 2005/0281913 A1* | 12/2005 | van Krieken et al. ............ 426/25 |
| 2009/0093034 A1* | 4/2009 | Uyama et al. ................. 435/139 |
| 2010/0016628 A1* | 1/2010 | Uyama et al. ................. 560/182 |
| 2010/0143966 A1* | 6/2010 | Singh et al. ..................... 435/41 |

FOREIGN PATENT DOCUMENTS

| JP | H0221599 | 1/1990 |
| JP | H05227884 | 9/1993 |
| JP | 2006042673 | 2/2006 |
| JP | 3854269 | 12/2006 |
| JP | 2006327893 | 12/2006 |
| JP | 2008174772 | 7/2008 |
| JP | 2009073793 | 4/2009 |
| WO | WO 2006124633 A1 * | 11/2006 |

OTHER PUBLICATIONS

European Search Report and the Written Opinion of the European Patent Office Patent Office in counterpart foreign application No. PCT/EP2010/065395 filed Oct. 14, 2010.
Enhancement of solvents production by *Clostridium acetobutylicum* cultivated on a reducing compounds depletive medium J. Ballongue, J. Amine, H. Petitdemange, R. Gay, Laboratoire de Chimie Biologique 1, Université de Nancy 1, BP 239, 54506—Vandoevre les Nancy Cédex, France, Received Mar. 17, 1986. Available online Jun. 25, 2003.
Proteomic insights into adaptive responses of *Saccharomyces cerevisiae* to the repeated vacuum fermentation. Cheng JS, Zhou X, Ding MZ, Yuan YJ. Source Tianjin University, People's Republic of China. *Appl Microbiol Biotechnol*. Jul. 2009;83(5):909-23. Epub Jun. 2, 2009.
Yanchevskii: "Composition of semi-manufactured products during single-phase vacuum processing of molasses mash (Translated)" Fermentnaya I Spirtovaya Promyshlennost (Ukraine), vol. 3, 1984, pp. 6-9, XP008125515.
Glycerol production by anaerobic vacuum fermentation of molasses on pilot scale P. D. Virkar, M. S. Panesar Article first published online: Feb. 18, 2004, Biotechnology and Bioengineering, vol. 29, Issue 6, pp. 773-774, Apr. 20, 1987.
Database Biosis [Online] Biosciences Information Service, Philadelphia, PA, US; 1990, Sakaguchi et al: "The influence of reduced pressure on the growth of yeast cells and the production of volatile compounds / Hakkokogaku Kaishi; 68(4), pp. 261-266, 1990" XP002597143 Database accession No. PREV199090085949.
Van Den Bosch et al / Wageningen University: "Growth of Caldicellulosiruptor saccharolyticus under reduced pressure" p. 1, XP002597144 Retrieved from the Internet: URL:www.biohydrogen. nl/downloadattachment/20602/posterfonsstam2.pdf [retrieved on Aug. 18, 2010].
State Intellectual Property Office of the People's Republic of China, Notification of the First Office Action in the corresponding Chinese Application 201080045842.9, date of notification Aug. 1, 2013.
Ma Hui, "Study on fermentation process for producing propionic acid", China Master's Theses Full-Text Database, 2010, No. 5.
Notice of Reasons for Rejection issued in corresponding Japanese Patent Application No. 2012-533629, dated Feb. 3, 2015 (four pages).
Takashima: "Fundamental Study of Low-Pressure Operation for Anaerobic Fermentation of Glucose" Journal of Japan Society on Water Environment, vol. 9, No. 10, pp. 621-626, published Oct. 5, 2006 (8 pages).

\* cited by examiner

*Primary Examiner* — Anand Desai
*Assistant Examiner* — Samuel Liu
(74) *Attorney, Agent, or Firm* — Westman, Champlin & Koehler, P.A.

(57) ABSTRACT

A fermentation process includes contacting a carbohydrate source with a microorganism in an aqueous fermentation broth to form a fermentation product which is a salt or a product with a boiling point above the boiling point of water. The fermentation process is carried out at a pressure which is below atmospheric pressure and at least at the value where the reaction medium is at its boiling point at the fermentation temperature. Water is evaporated and removed from the reactor during the fermentation in an amount which is at least 20% of the volume of liquid present in the reactor at the start of the fermentation. A fermentation process at reduced pressure while removing a substantial amount of water removes a surplus of water in the system, ensures removal of reaction heat, and may lead to improved fermentation quality.

19 Claims, No Drawings

FERMENTATION PROCESS AT REDUCED PRESSURE

CROSS-REFERENCE TO RELATED APPLICATION

This Application is a Section 371 National Stage Application of International Application No. PCT/EP2010/065395, filed Oct. 14, 2010 and published as WO 2011/045365A1 on Apr. 21, 2011, in English.

BACKGROUND

The discussion below is merely provided for general background information and is not intended to be used as an aid in determining the scope of the claimed subject matter.

Fermentation processes are well known in the art. They are used to manufacture a number of different components such as acids, including lactic acid, acetic acid, propionic acid, and succinic acid, alcohols, such as ethanol, propanol, butanol, and erythritol, and numerous other components of biological origin such as vitamins.

In the art, there is a continuous need for improved fermentation processes.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

An aspect of the present invention pertains to a fermentation process wherein a carbohydrate source is contacted under fermentation conditions with a microorganism in an aqueous fermentation broth to form a fermentation product which is a salt or a product with a boiling point above the boiling point of water, wherein the fermentation process is carried out at a pressure which is below atmospheric pressure and at least at the value where the reaction medium is at its boiling point at the fermentation temperature, with water being evaporated and removed from the reactor during the fermentation in an amount which is at least 20% of the volume of liquid present in the reactor at the start of the fermentation.

Another aspect of the present invention is that the fermentation process is carried out at reduced pressure, that is, at a pressure below atmospheric pressure, resulting in the evaporation and removal of a substantial amount of water. The lower limit of the pressure is provided by the consideration that the reaction medium should be in the liquid phase under fermentation conditions. This means that at the fermentation temperature the pressure should be such that the fermentation medium is at its boiling temperature, or higher. This will be discussed in more detail below.

DETAILED DESCRIPTION OF THE ILLUSTRATIVE EMBODIMENTS

The present disclosure solves the problem of a surplus of water associated with some fermentation processes known in the art. In a fermentation process the feed source, generally a carbohydrate source, is added to the reactor in combination with water, for example in dissolved form. Further, additional streams such as pH regulating agents may sometimes be added, again in the form of aqueous solutions. This may lead to the formation of dilute product streams, which may necessitate the use of water removal steps, e.g., during the process. However, this has a number of disadvantages. In the first place, where reaction medium is removed, this may be associated with the removal of liquid product, which leads to a yield loss in the process. Further, when the volume of water removed during or after the fermentation is large, this requires the use of large apparatus which, by its nature, is expensive. Accordingly, there is need for a fermentation process which reduces the surplus water in the fermentor in a cost-effective way.

It has now been found that this problem can be solved in an elegant manner by carrying out the fermentation under reduced pressure. The reduction of pressure leads to an increased evaporation of water which is then removed, and therewith to more concentrated product streams.

A further advantage of the process described herein resides in the removal of heat generated during the fermentation.

Conventionally, fermentation processes are carried out at constant temperature. The heat generated during the fermentation needs to be removed from the system. In the disclosed process the application of a vacuum results in evaporation of liquid, and this leads to the removal of heat from the system. Accordingly, it is an advantage of the disclosed process that it reduces the need for removal of heat generated during the fermentation process.

To keep the fermentation temperature at the required value, it may be necessary to provide additional heat to the system. When low quality waste heat is used to provide this additional heat, the disclosed process can be carried out in a process-efficient manner. Suitable low quality waste heat may derive from the fermentation process itself, from concentration steps further on in the procedure, or from other available sources. Therefore, in one embodiment, the process can be provided with low quality waste heat. Within the context of the present specification, the wording low quality waste heat refers to heat derived from hot utility streams with a temperature of below 100° C., more in particular below 70° C. The use of streams with a supply temperature between 5 and 25° C. above the fermentation temperature, more in particular between 5 and 15° C. is particularly attractive.

It is noted that fermentation processes have been described in the art wherein a reduced pressure is applied to remove a reaction product with a higher volatility than water, and wherein co-evaporated water is partly condensed and fed back to the reaction vessel, e.g., using a condensor. It will be evident to the skilled person that where the present specification mentions that water is removed, it is meant that it is indeed removed, and not evaporated, condensed, and fed back directly to the reactor.

It is a further feature of the present disclosure that an increased yield of fermentation product may be obtained as compared to fermentation systems where water is removed through other means, e.g., as a side stream. This may go for either or both of the yield of desired product per gram substrate and the yield of desired product per liter fermentation medium. This is because removal of the surplus water through evaporation as a result of the application of reduced pressure is not accompanied by removal of fermentation product, in contrast with removal through other means, e.g., as a side stream. Further, because in the disclosed process the water is removed through evaporation, the water stream removed from the reactor may not require additional purification.

Additionally, it has been found that the disclosed process may lead to an improved fermentation quality. Not wishing to be bound by any theory it is suspected that the application of reduced pressure may result in the evaporation of low-boiling contaminants which inhibit the microorganism, or which cause off-odors, off-flavors, or other undesirable properties in the final product.

The process described herein is applicable to the formation of fermentation products which are salts, or which have a boiling point above the boiling point of water. If the fermentation product has a boiling point below the boiling point of water, it will be evaporated and removed with the water at reduced pressure. This does not solve the problem underlying the present disclosure, which is the provision of a fermentation broth with reduced water content and increased product yield.

The process described herein finds application in numerous types of fermentation processes. It has been found to be particularly suitable for the fermentation processes which are carried out under anaerobic conditions.

Suitable products that may be manufactured via the disclosed process include organic acids (or the salts thereof), such as lactic acid, acetic acid, propionic acid, and succinic acid, alcohols, such as butanol, and erythritol, and numerous other components of biological origin such as vitamins. The manufacture of organic acids as main product is preferred, with the manufacture of lactic acid and succinic acid (or the salts thereof) being particularly preferred.

In the disclosed process it is intended that fermentation product or products towards which the fermentation is aimed, also indicated as the main fermentation products, are salt(s) and/or have a boiling point above the boiling point of water. That is, they are to remain in the fermentation medium in liquid or solid form. This does not exclude the formation of by-products which are not salts and have a boiling point below the boiling point of water, and which will thus be removed in whole or in part during the fermentation process due to the application of the vacuum. The total yield of main fermentation product (or products) will generally be at least 20 wt. %, calculated as gram of product per gram of converted substrate, in particular, at least 30 wt. %, more in particular at least 50 wt. %. Depending on the nature of the fermentation, the total yield of main fermentation product (or products) may be at least 60 wt. %, calculated as gram of product per gram of converted substrate, sometimes at least 80 wt. %, more in particular at least 80 wt. %, or even at least 90 wt. %.

It is noted that the disclosed process is not directed to fermentation processes aimed at the manufacture of ethanol, wherein the total of ethanol and carbon dioxide makes up 70 wt. % or more of the product, calculated on the amount of converted substrate. It is noted that the present disclosed is not directed to fermentation processes wherein hydrogen is the main product.

As discussed above, the fermentation is carried out at a pressure which is below atmospheric pressure. The minimum pressure at which the process can be carried out is determined by the fermentation temperature. The pressure should be at least so high that the fermentation medium is at or below its boiling point. If temperature of the fermentation medium is above its boiling point, the fermentation medium will vaporize and the temperature will drop until the medium is at its boiling point. In other words, the minimum pressure for the disclosed process is the vapor pressure of the liquid at fermentation temperature.

The boiling point of a reaction medium is the temperature at which the vapor pressure of the liquid equals the environmental pressure surrounding the liquid. Boiling is the process in which molecules anywhere in the liquid escape into the vapor phase, resulting in the formation of bubbles in the liquid. The boiling point may also be indicated as the saturation temperature, namely the temperature where the liquid, at a given pressure, is saturated with thermal energy, and wherein the addition of any energy will result in a phase transition.

The fermentation will be effected at a fermentation temperature which is selected on a case by case basis. Considerations include maximum yield of the desired product and maximum conversion. It is within the scope of the skilled person to select appropriate conditions. The temperature may vary over the fermentation process, for example to optimize growth at the beginning of the process and yield nearer the end of the process. This may result in the variation of fermentation pressure.

Incidentally, it should be noted that surprisingly it has been found possible to carry out the disclosed process at a pressure at which the fermentation medium boils. Apparently, the microorganism is not detrimentally affected by being surrounded by a boiling medium. Accordingly, it is a possibility for the pressure to be selected such that the aqueous fermentation medium boils at the temperature at which fermentation is carried out.

The pressure applied in the disclosed process is below atmospheric pressure, to increase evaporation of water as compared to a process carried out at atmospheric pressure. For example, the pressure may be selected to be between 20 mbar and 950 mbar, more in particular between 40 and 500 mbar.

In the disclosed process water is evaporated and removed from the reactor during the fermentation in an amount which is at least 20% of the volume of liquid present in the reactor at the start of the fermentation. If the amount of water which is removed is less, the advantages associated with the disclosed process may not be obtained to such an extent that they balance the costs associated therewith. The amount of water that is desired to be removed will depend on a number of features. One feature is the concentration of the substrate steam. If the substrate is provided in a relatively dilute form, e.g., for cellulose hydrolysates, it will be desirable to remove more water than when the substrate is provided in a more concentrated form. If a dilute stream is added during the fermentation, e.g., a dilute stream of a pH regulating agent such as a base, it will be desirable to remove more water than when no such stream is provided, or when a more concentrated stream is provided. The upper limit for the amount of water removed will depend on the amount of water remaining in the reaction vessel. This should be sufficient to allow proper mixing of the reactor. It is within the scope of the skilled person to determine the suitable amount of water to be removed, taking the above into account.

Depending on these various parameters, the amount of water removed during the fermentation may be at least 40% of the volume of liquid present in the reactor at the start of the fermentation, more in particular at least 50%. In the case of dilute substrate streams or other liquids provided to the reactor, the amount of water may be much higher, e.g., at least 75%, or in some cases at least 100%.

In general, the amount of water removed in the process is regulated by selecting the time during which the pressure is reduced and the amount of heat that is supplied to the fermentation medium. Taking the above into account it is within the scope of the skilled person to select the fermentation conditions such that the desired amount of water is removed.

In one embodiment, water is added during the fermentation, as will be discussed in more detail below. In this embodiment it may be preferred for the pressure to be selected such that the volume of water removed from the reactor by evaporation is at least 1%, in particular at least 5%, more in particular at least 10% of the total of water added during the fermentation. In this embodiment the volume of water removed is often at most 50% of the total of water added during the fermentation.

In some fermentation processes, aqueous solutions are added during the fermentation, for example to add pH control agents or in fed batch processes. In these processes, the removal of water may be of particular interest, because in some cases the amount of water added during fermentation may be quite substantial. As an example the situation may be mentioned where a high substrate concentration inhibits the fermentation, but where the product does not, for example because it is solid.

In one embodiment the disclosed process pertains to a fermentation process to manufacture a product comprising a salt of an acid. In these fermentation processes, the microorganism produces an acid, and a solution of a base is added to the fermentation medium to keep the pH within the range required for the microorganism at issue, converting the acid in whole or in part to its corresponding salt. This base addition may be accompanied by the addition of undesirably large amounts of water.

Acids that may be manufactured via the process disclosed herein include carboxylic acids, in particular carboxylic acids selected from the group consisting of mono-, di-, and tricarboxylic acids having 2-8 carbon atoms. Examples include lactic acid, propionic acid, citric acid, malic acid, maleic acid, fumaric acid, adipic acid, succinic acid, tartaric acid, alpha-ketoglutaric acid, oxaloacetic acid, acetic acid, and acrylic acid, or salts thereof. At this point in time fermentation processes aimed at manufacturing lactic acid or succinic acid or salts thereof are considered preferred.

In one embodiment according to the disclosed process, a fermentation procedure is used wherein the product aimed for is in the form of its salt, or has a boiling point above that of water, while a main byproduct has a boiling point below that of water. In this case performing the fermentation under reduced pressure ensures the removal of substantial amounts of the undesirable byproduct. An example of this type of fermentation would be a mixed acid fermentation where the formation of acid, in particular acetic acid, is accompanied by the production of ethanol.

As discussed above, during the fermentation, the formation of acid results in a decrease in the pH. To counter this and keep the pH within the range where the microorganism can perform, a basic solution is typically added during the fermentation. Suitable basic solutions contain solutions comprising one or more of calcium oxide, calcium hydroxide, calcium carbonate, calcium bicarbonate, magnesium oxide, magnesium hydroxide, sodium hydroxide, ammonium hydroxide, potassium hydroxide, magnesium carbonate, sodium bicarbonate, potassium bicarbonate. Depending on the solubility of the base, the basic solution mentioned above may be a true solution in the sense that the base is completely dissolved and the solution does not contain solid components. However, the basic solution may also be a slurry, which contains solid particles in addition to dissolved base. Within the present specification the word solution is intended to encompass both embodiments.

Generally, the basic solution is added in an amount effective to control the pH of the broth between about 3 and 9, more specifically between 5.5 and about 7.0.

It has been found that solutions of magnesium salts, in particular solutions of magnesium hydroxide, have to be relatively dilute to allow adequate pumpability. Accordingly, in this case, the concentration of the basic solution will be relatively low, as a result of which a relatively large amount of water is added.

Accordingly, in one embodiment, the disclosure pertains to a process for fermentative manufacture of an acid where a basic solution of a magnesium salt is used to keep the pH in a predetermined range.

The manufacture of lactic acid is a preferred embodiment of the present disclosure. Accordingly, in one embodiment, the present disclosure pertains to a process for manufacturing lactic acid wherein a carbohydrate source is contacted under fermentation conditions with a microorganism suitable for the production of lactic acid in an aqueous fermentation broth to form a lactic acid fermentation product, while a basic solution is added to the fermentation broth during fermentation to keep the pH in a predetermined range.

Fermentative lactic acid manufacture is well known in the art. The following description is given as general elucidation only.

The carbohydrate source in, e.g., lactic acid manufacture generally comprises one or more of sugars, (liquefied) starch, sugar syrup, or cheese whey, glucose, fructose, or galactose, or disaccharides such as sucrose or lactose, hexoses and pentoses in hydrolysates of plant origin, such as biowaste, wood, straw, etc.

Suitable microorganisms include *Lactobacillus* sp. such as *L. delbrueckii, Bacillus coagulans, Bacillus thermoamylovorans, Bacillus smithii, Geobacillus stearothermophilus*, and *Escherichia Coli*.

Each microorganism has its own optimum pH and temperature range. The pressure that may be used depends on the optimum temperature for the microorganism.

If so desired, enzymes may be added during the fermentation process to help convert the carbohydrate source into compounds which can be processed by the microorganism.

It is within the scope of the skilled person to select an appropriate combination of substrate, microorganism, and reaction conditions to obtain a fermentation process suitable for use in the disclosed process.

In one embodiment of the disclosed process, the fermentation is a simultaneous saccharification and fermentation (SSF) process wherein a feed is contacted with a microorganism and an enzyme.

In a simultaneous saccharification and fermentation process, a low-value feed source is subjected to enzymatic processing to produce sugar, which is simultaneously fermented to the final fermentation product, e.g., lactic acid, using a microorganism. It has been found that an SSF process is an attractive candidate for fermentation under reduced pressure, because in this process undesirable byproducts resulting from the enzymatic reaction are at least partly removed from the system by volatilisation.

The low-value feed source may be selected from starch and partial hydrolysates of starch, the latter also known as liquefied starch, malto-dextrines or maltooligosaccharides. Suitable enzymes that may be added to the fermentation medium include one or more of alpha-amylases or glucoamylases or pullulanase. Alternatively, the low-value feed source may be selected from cellulose-containing materials, such as biowaste. In this case, suitable enzymes include cellulases.

Accordingly, in one embodiment, the present disclosure pertains to a method for the production of lactic acid or a salt thereof wherein a low-value feed source is subjected to a process of simultaneous saccharification and fermentation, the method comprising saccharifying the low-value feed source in a medium comprising at least an enzyme capable of converting the low-value feed source to a sugar component, and simultaneously fermenting the sugar component using a microorganism, and optionally isolating lactic acid from the medium, wherein the fermentation process is carried out at a pressure which is below atmospheric pressure and at least at a value where the reaction medium is at its boiling point at the fermentation temperature.

For further information on a suitable SSF process, in particular a process where the low-value feed source is selected from starch and partial hydrolysates of starch, the latter also known as liquefied starch, malto-dextrines or maltooligosaccharides and suitable enzymes that may be added to the fermentation medium include one or more of alpha-amylases or glucoamylases or pullulanase, reference is made to WO03095659, the disclosure of which is incorporated herein by reference.

In general, the use of reduced pressure does not affect the properties and conditions of the fermentation. Accordingly, the disclosed process may be applied to any fermentation process wherein it is desired to reduce water content of the fermentation product and increase product yield.

It is within the scope of the skilled person to determine whether a particular fermentation procedure can suitably be adapted by applying the disclosed process. Further elucidation is not required.

The present disclosure will be elucidated by the following example, without being limited thereto or thereby.

Example 1

A 7 liter stirred fermenter was equipped with an external condenser coupled to the head space. The condenser was kept at 4° C. with a cryostate. The fermenter and condenser could be evacuated with a vacuum pump. In the fermenter, a fermentation medium was prepared containing 1000 grams of sucrose and 2700 grams of demineralised water. Diammonium phosphate and diammonium sulphate were added as nitrogen source. Vitamins and trace elements were added as is conventional in the art.

A 10% inoculum of a lactic acid producing microorganism was added to the fermentation medium and the fermentation medium was brought to reaction temperature of 55° C. The microorganism produced lactic acid. The pH of the medium was continuously monitored and maintained at a value of 6.4 by addition of a slurry of magnesium hydroxide.

After 24 hours, the pressure above the fermentation medium was reduced, to a value of 120 mbar. The temperature of the fermentation medium was maintained at 55° C. It was observed that the fermentation medium boiled during the fermentation. However, the lactic acid production profile appeared to be comparable to a fermentation at atmospheric conditions. In 6 hours, 1800 ml of water was evaporated and condensed in the external condenser. The fermentation was left to proceed. When all sugar was consumed, the fermentation broth had a volume of 3200 ml. As compared to a conventional atmospheric fermentation, performing the fermentation at reduced pressure resulted in a reduction of the volume of the fermentation liquid by almost 50%. Additionally, the yield of the fermentation, in grams of solid magnesium lactate per liter final fermentation broth, was found to have increased.

In this example the amount of water being evaporated and removed from the reactor during the fermentation is 67%, calculated on the volume of liquid present in the reactor at the start of the fermentation.

Example 2

A 70 liter stainless steel stirred fermenter was equipped with an external plate and frame condenser and condensate collection vessel coupled to the head space. The fermenter and condenser could be evacuated with a variable drive membrane vacuum pump. The fermenter was double walled and was kept at the desired temperature with a water-heating bath. In the fermenter, a fermentation medium was prepared containing 18 kg of sucrose and 50 L of demineralised water. Diammonium phosphate and diammonium sulphate were added as nitrogen source. Vitamins and trace elements were added as is conventional in the art.

5.8 L inoculum of a lactic acid producing microorganism was added to the fermentation medium and the fermentation medium was brought to the reaction temperature of 55° C. The microorganism produced lactic acid. The pH of the medium was continuously monitored and maintained at a value of 6.4 by addition of a 20.7 wt % magnesium hydroxide slurry.

After 18 hours, the pressure above the fermentation medium was reduced, to a value of 110-125 mbar. This pressure was maintained by a digital vacuum meter coupled to the vacuum pump. The temperature of the fermentation medium was maintained at 55° C. by a temperature probe coupled to the water-heating bath. The condenser was kept at 20° C. with cooling water. It was observed that the fermentation medium boiled during the fermentation. 100 ml of antifoaming agent was added to reduce foaming. After 14 hours, 32 L of water had been evaporated and condensed in the external condenser. The lactic acid production profile remained comparable to fermentation at atmospheric conditions. When all sugar was consumed, the fermentation broth had a volume of 66 L. As compared to a conventional atmospheric fermentation, performing the fermentation at a reduced (vacuum) pressure resulted in a reduction of the liquid volume of the fermentation broth by about 43%. The yield of the fermentation, in grams solid magnesium lactate per liter final fermentation broth, was found to have increased. The total amount of lactate produced by the fermentation process performed under reduced pressure was comparable to the total amount produced by a comparable process carried out under atmospheric conditions.

In this example the amount of water being evaporated and removed from the reactor during the fermentation is 64%, calculated on the volume of liquid present in the reactor at the start of the fermentation.

The invention claimed is:

1. A method of producing carboxylic acid which boiling point is above the boiling point of water by a fermentation process with increased yield of produced carboxylic acid as compared to a conventional atmospheric fermentation wherein the yield is calculated as gram of product per gram of converted substrate; the method comprises contacting a carbohydrate source under fermentation conditions in a reactor with a microorganism capable of producing said carboxylic acid in an aqueous fermentation broth; and adding a basic solution to the fermentation broth during fermentation of said producing carboxylic acid to keep the pH in a predetermine range; wherein the fermentation process is carried out at a pressure which is below atmospheric pressure carried out at a fermentation temperature which is at the boiling point of fermentation broth under said pressure wherein said temperature allows the microorganism to produce said carboxylic acid, and wherein under said pressure water is evaporated and removed from the reactor during the fermentation in an amount which is at least 20% of the volume of liquid present in the reactor at the start of the fermentation thereby producing the carboxylic acid with the increased yield.

2. The fermentation process according to claim 1, wherein the pressure is selected such that the aqueous fermentation broth boils at the temperature at which fermentation is carried out.

3. The fermentation process according to claim 1 wherein water is added during the fermentation and the pressure is selected such that the volume of water evaporated and removed from the reactor is at least 1% of the total of water added during the fermentation.

4. The fermentation process according to claim 1, wherein the acid fermentation product comprises one or more carboxylic acids selected from the group consisting of mono-, di-, and tricarboxylic acids having 2-8 carbon atoms.

5. The fermentation process according to claim 4, wherein the acid fermentation product comprises lactic acid or succinic acid or salts thereof.

6. The fermentation process according to claim 4, wherein the acid fermentation product comprises lactic acid or a salt thereof.

7. The fermentation process according to claim 1, wherein the basic solution comprises one or more of calcium oxide, calcium hydroxide, calcium carbonate, calcium bicarbonate, magnesium oxide, magnesium hydroxide, sodium hydroxide, and potassium hydroxide.

8. The fermentation process according to claim 1, wherein the fermentation process is a simultaneous saccharification and fermentation process wherein a feed is contacted with a microorganism and an enzyme.

9. The fermentation process according to claim 1 wherein water is added during the fermentation and the pressure is selected such that the volume of water evaporated and removed from the reactor is at least 5% of the total of water added during the fermentation.

10. The fermentation process according to claim 1 wherein water is added during the fermentation and the pressure is selected such that the volume of water evaporated and removed from the reactor is at least 10% of the total of water added during the fermentation.

11. The fermentation process according to claim 1, wherein the basic solution comprises magnesium hydroxide.

12. The fermentation process according to claim 1, wherein acid fermentation product comprises one or more carboxylic acids selected from lactic acid, propionic acid, citric acid, malic acid, maleic acid, fumaric acid, adipic acid, succinic acid, tartaric acid, alpha-ketoglutaric acid, oxaloacetic acid, and acetic acid, or salts thereof.

13. A method of producing carboxylic acid which boiling point is above the boiling point of water by a fermentation process with increased yield of produced carboxylic acid as compared to a conventional atmospheric fermentation wherein the yield is calculated as gram of product per gram of converted substrate; the method comprises:
   combining a carbohydrate source with a microorganism in a reactor to form an aqueous fermentation broth;
   adjusting a temperature of the aqueous fermentation broth such that fermentation occurs to produce carboxylic acid which boiling point is above the boiling point of water;
   adding a basic solution to the fermentation broth to maintain a pH of the fermentation broth within a selected pH range between 5.5 and 7.0 while the fermentation for said production is carried out;
   adjusting a pressure to below atmospheric pressure in the reactor such that the fermentation is carried out at the temperature which is equal to the boiling point of the aqueous fermentation broth; and
   evaporating water from the aqueous fermentation broth while the fermentation for producing said carboxylic acid is carried out such that at least 20% of the volume of liquid present in the reactor at the start of the fermentation is removed from the reactor thereby producing the carboxylic acid with the increased yield.

14. The fermentation process according to claim 13, wherein the acid fermentation product comprises a salt.

15. The fermentation process according to claim 13, wherein the acid fermentation product comprises one or more carboxylic acids selected from the group consisting of mono-, di-, and tricarboxylic acids having 2-8 carbon atoms.

16. The fermentation process according to claim 13, wherein the acid fermentation product comprises lactic acid or succinic acid or salts thereof.

17. The fermentation process according to claim 13, wherein and further comprising:
   adding an enzyme with the microorganism such that the process is a simultaneous saccharification and fermentation process.

18. The fermentation process according to claim 13, wherein the basic solution comprises one or more of calcium oxide, calcium hydroxide, calcium carbonate, calcium bicarbonate, magnesium oxide, magnesium hydroxide, sodium hydroxide, and potassium hydroxide.

19. The fermentation process of claim 13, wherein the basic solution comprises magnesium hydroxide.

* * * * *